United States Patent [19]

Bielewicz

[11] Patent Number: 5,090,249

[45] Date of Patent: Feb. 25, 1992

[54] APPARATUS AND METHOD FOR TESTING THE MECHANICAL PROPERTIES OF A SAMPLE

[76] Inventor: Jerzy Bielewicz, 106-99 Dalhousie Drive, Winnipeg, Manitoba, Canada, R3T 3M2

[21] Appl. No.: 564,352

[22] Filed: Aug. 8, 1990

[51] Int. Cl.⁵ .............................................. G01N 11/00
[52] U.S. Cl. ..................................................... 73/822
[58] Field of Search ................................ 73/787–793, 73/813, 811, 818–825

[56] References Cited

U.S. PATENT DOCUMENTS

| | | | |
|---|---|---|---|
| 1,695,046 | 12/1928 | Hippensteel | 73/790 |
| 2,049,644 | 8/1936 | Essen | 73/790 |
| 3,443,423 | 5/1969 | Lou Ma | 73/821 |
| 4,137,757 | 2/1979 | Kovacs | 73/818 |
| 4,313,289 | 2/1982 | Birdsong, Jr. | 73/818 |
| 4,972,719 | 11/1990 | Vinson et al. | 73/790 |

FOREIGN PATENT DOCUMENTS

| | | | |
|---|---|---|---|
| 0139641 | 8/1982 | Japan | 73/818 |
| 0565252 | 7/1977 | U.S.S.R. | 73/790 |

OTHER PUBLICATIONS

Smirnov et al., "Device for the Quick Analysis of the Mechanical Properties of Damp Pellets", Ind. Lab. (U.S.A.), vol. 39, No. 4 (Apr. 1973).

*Primary Examiner*—Robert Raevis
*Attorney, Agent, or Firm*—Adrian D. Battison; Stanley G. Ade; Murray E. Thrift

[57] ABSTRACT

Creep/recovery tests of a small sample are carried out on a conventional testing machine with vertical compression capabilities using an additional spring which allows the drive system of the testing machine to apply the force to the small sample substantially instantaneously and then to maintain that force substantially constant as required for a creep/recovery test. The addition of the spring allows the drive system to be halted at the predetermined required force with high accuracy. The spring is selected to have a large deformation relative to the deformation of the sample during the creep period so that the force is maintained substantially constant irrespective of the creep deformation of the sample. For the first time this arrangement allows creep/recovery tests of small samples such as seeds to be carried out.

8 Claims, 3 Drawing Sheets

APPARATUS AND METHOD FOR TESTING THE MECHANICAL PROPERTIES OF A SAMPLE

BACKGROUND OF THE INVENTION

This invention relates to an apparatus and method for testing the mechanical properties of a sample and particularly of a sample which is either relatively small in size or of a material which has a very steep force versus deformation characteristic.

Standard equipment is available for testing the stress and strain characteristics of a sample. In such devices a force or stress is applied to the sample and the deformation or strain is then detected so that calculations can be made on the properties of the material forming the sample depending upon the results of various test parameters.

For many years fundamental tests have been available to measure the properties that are inherent to the material under test and do not depend upon the geometry of a tested sample, the conditions of loading or the apparatus. Examples of these properties are modulus of elasticity, poisson's ratio, relaxation and retardation time, sheer modulus, etc.. The fundamental tests as applied to any sample material may be classified into two essentially different groups; those conducted under conditions of static or quasi-static loading, and those conducted under dynamic conditions.

Machines have been available for many years to carry out such testing often known as a universal testing machine such as those manufactured by Instron or Chatillon.

There are a number of tests developed which may be used to study visco-elastic materials such as biological materials and determine their relations between stress, strain and time for given type of deformation and a given type of loading pattern. The most important tests include stress-strain, creep-recovery, stress-relaxation and dynamic tests.

In creep-recovery tests, the load is suddenly applied and held constant for a given period of time and then removed. In this test the deformation is measured as a function of time. Rheological models are available to calculate constant characteristics for the material from these tests.

In a further series of tests, the deformation relative to time can be determined for a plurality of cycles of repeated cycles of loading and unloading of the sample.

In all these tests it is necessary to apply to the sample a predetermined maximum force. For creep-recovery tests the rate of loading must be relatively rapid since the formulae assume that the loading is applied substantially instantaneously.

One machine which is available for these tests is known as a Universal Tester Model ET1100 manufactured by John Chattilon & Sons Inc. of New York. This machine includes an upper transverse bar which is fixed to a structural frame and a lower transverse bar which is movable in a vertical direction under very accurate control from a pair of lead screws driven by a constant velocity motor. A first and a second sample engagement plate are mounted on the upper and lower bars respectively and adjusted so that they lie parallel and at right angles to the direction of movement of the bar. The sample is then positioned between the plates so that it is compressed by upward movement of the bar. A load cell can be positioned between the upper plate and the upper bar to determine the force applied to the sample. The deformation of the sample is measured by detecting the location of the movable lower bar through the control system moving the lower bar.

This device is well known and is a standard machine available in many testing laboratories for carrying out the standard tests. The machine is entirely satisfactory and highly accurate for many operations where the sample is relatively large and where the sample is relatively resilient so that the deformation of the sample is relatively large in comparison with the force applied.

The above prior art machine uses a lead screw drive system for the accurate control of the bar movement. Other prior art machines for example manufactured by Instron use a hydraulic drive system for this accurate control. The present invention is concerned with both types of machine.

Up till now however the standard machine has been entirely unsuitable for carrying out tests on very small samples such as those less than five millimeters in diameter or in carrying out tests on samples in which the deformation is very small thus causing the force to increase very rapidly.

The problem with the machine in its standard form is that it is necessary for the tests to set a maximum force or predetermined force to which the machine will move and will then halt. Unfortunately when the deformation involved is very small, the feedback between the load cell and the motor is insufficiently accurate to ensure that the machine stops at the predetermined force. This predetermined force can in such cases vary significantly by as much ten or twenty percent leading of course to completely inaccurate results. The machine and the standard tests defined for the machine provide no solution to this problem and accordingly the machine has generally been considered to be unsatisfactory for testing of small samples or samples where the force increases dramatically for small deformation so that the movement of the device is insufficiently controlled to accurately limit the maximum force to be applied. Thus it has been impossible to perform creep-recovery tests with this machine up till now.

An alternative machine is available which uses a beam along which a load moves at a constant velocity so that the force applied to a sample upon which the beam rests increases at a constant rate provided the load moves along the beam at a constant rate. In theory this machine should allow very accurate control of the maximum force. This machine also allows the increase of that force up to the maximum at a constant rate.

However, in practice the load must be halted at a particular location along the beam and of course the momentum of the load causes a dynamic impact at the point of halting of the load and this interferes with the accurate testing of the sample.

At the present time, therefore, there is no machine available for carrying out these tests on the very small samples.

SUMMARY OF THE INVENTION

It is one object of the present invention, therefore to provide an improved method and apparatus for carrying out tests of this nature.

According to a first aspect of the invention, therefore, there is provided a method for testing the mechanical properties of a sample of a solid material comprising providing a first abutment member having first means thereon for engaging the sample, providing a second abutment member having second means thereon for engaging the sample, placing the sample between the abutment members for application thereto of force in a longitudinal testing direction, moving the second abutment member relative to the first abutment member in said longitudinal testing direction to apply stress to the sample to cause strain in the sample, and measuring the stress and strain for analysis of the mechanical properties of the sample, wherein the movement of the second abutment member is applied from a movable element through a spring located between the movable element and the second abutment member so as to communicate force therebetween, the spring being elastically deformed during said movement.

According to a second aspect of the invention, therefore, there is provided an apparatus for testing the mechanical properties of a sample of a solid material comprising a first abutment member having first means thereon for engaging the sample, a second abutment member having second means thereon for engaging the sample, such that the sample can be supported between the abutment members for application thereto of force in a longitudinal testing direction, means for moving the second abutment member relative to the first abutment member in said longitudinal testing direction to apply stress to the sample to cause strain in the sample, and means for measuring the stress and strain for analysis of the mechanical properties of the sample, wherein said moving means comprises a movable element, and a spring located between the movable element and the second abutment member so as to communicate force therebetween, the spring being elastically deformed during said movement.

The new method is therefore based upon the compression of the investigating material with a constant rate of loading of the force. This is achieved in the present apparatus by the use of the spring which is connected in series with the material under investigation. In such a situation, the force acting on the specimen is equal to the force acting on the spring. If the properties of the spring are selected so they are closely related to the expected mechanical properties of the investigative material and therefore the deformation of the spring is large in comparison to the deformation of the investigative material, the force versus time characteristics for the investigative material during loading and unloading process will follow a straight line relationship which is specific for the spring. The rate of loading and unloading may be changed by changing the speed of the movable element.

The new method can be used for creep and recovery tests on a single small sample. The major advantage of the new method is that minute deformation of the investigative material is translated to a large deformation of the spring. This provides a very sophisticated control over the applied force. The problem of dynamic impact inherited by and unsolved in other methods is completely eliminated in the new method.

With the foregoing in view, and other advantages as will become apparent to those skilled in the art to which this invention relates as this specification proceeds, the invention is herein described by reference to the accompanying drawings forming a part hereof, which includes a description of the best mode known to the applicant and of the preferred typical embodiment of the principles of the present invention, in which:

DETAILED DESCRIPTION

Figure 1:
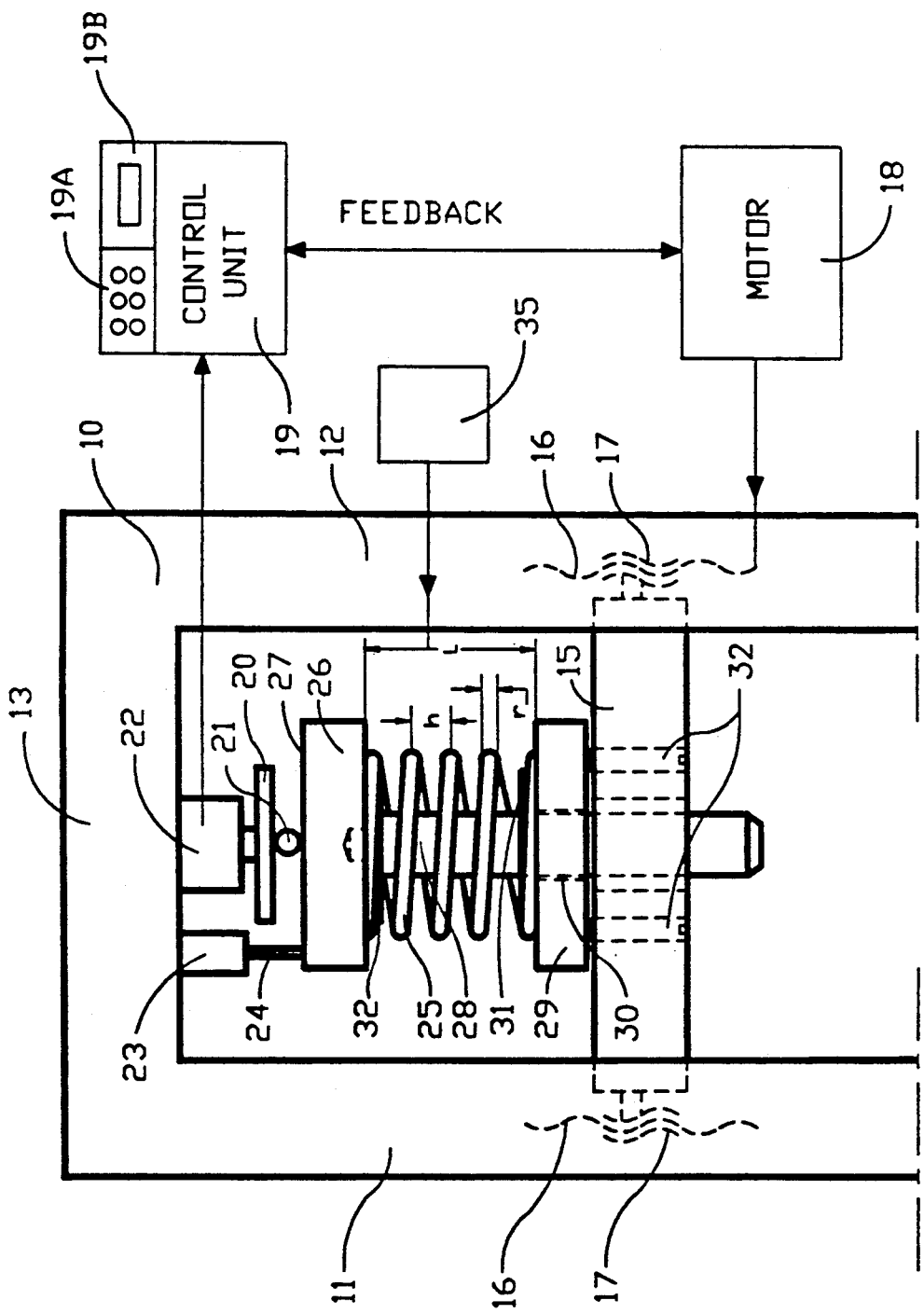
FIG. 1 is a schematic front elevational view of an apparatus according to the present invention omitting those features of the device which are conventional.

The basic machine is not shown in complete detail as full details of the machine will be well known to one skilled in the art. One example of a universal testing machine of the type to which the present invention relates is that manufactured by John Chatillon & Sons Inc. of Vew Gardens New York and full details of this machine are set out in the manual operation of the machine. Basically the machine includes a main support frame 10 including a pair of vertical struts 11 and 12 and a horizontal top beam 13 which are supported upon a suitable base structure so as to be maintained in fixed location.

The machine further includes a lower beam 15 which is supported so as to lie directly parallel to the upper beam 13 and is movable in a vertical direction that is a direction at right angles to the upper and lower beams for carrying out the testing action. The lower beam is driven in its movement by a pair of lead screws 16 and cooperating nuts 17 carried upon the beam. The drive system is of highly accurate machined construction so that the movement of the lower beam 15 can be controlled very accurately so it takes place in a directly vertical direction without any twisting and so that it can be commenced and stopped at specific locations. In addition the speed of movement of the lead screws driven by a motor 18 under control of a controlled unit 19 is arranged to be very accurately constantly driven so that the movement of the beam is at a constant rate. This leads to a rate of deformation of the sample which is constant so that the rate of application of force varies.

The conventional machine further includes an upper abutment member 20 which comprises a plate for engaging a sample 21. Between the plate 20 and the beam 13 is provided a load cell 22. The plate 20 is thus fixed and remains at a constant location but the forces applied to the plate by the upward movement of the beam 15 can be accurately measured by the load cell 22 and communicated to the control unit for feedback to the motor to control the movement of the motor in dependence upon the force applied. The movement of the beam 15 relative to the upper plate 20 is detected by the control system for moving the lower beam thus providing a detection of the deformation of the sample 21.

In the conventional machine (not shown), the plate which engages the underside of the sample is directly physically attached to the beam 15 for movement therewith and this arrangement is considered in the original machine to be an essential construction so that accurate measurements are obtained.

In the present invention, however, the conventional machine described above is modified by the inclusion of a spring 25 which is mounted in series with the sample 21 between the upper plate 20 and the beam 15.

Specifically a lower abutment member 26 for engaging the underside of the sample comprises a substantially flat plate with a planar upper surface 27 parallel to the undersurface of the plate 20 for receiving the sample therebetween. The abutment member 26 is mounted upon a rod 28 with the rod extending rearwardly from the plate 26 and in a directly vertical direction. The rod is constrained to move in the vertical direction longitudinally of its axis by a further plate 29 having an opening 30 therein machined to just receive the periphery of the rod in a sliding action thus preventing the plate 26 from twisting and ensuring that it is maintained directly horizontal while moving vertically. The spring 25 is positioned between the underside of the plate 26 and the upper side of the plate 29. The spring is carefully machined so that it rests directly against the surfaces of the plates while the axis of the spring remains directly vertical so that the spring does not provide any twisting action on the plate 26 which might cause binding of the rod 28 in its guide surface 30. The spring can be mounted on the surfaces by way of bosses 31 and 32 to ensure that it is properly located and the system maintained for accurate movement. The plate 29 can be adjusted relative to the beam 15 by adjustment screws 32 so as to adjust the orientation of the upper surface 27 of the plate 26 to ensure that it is accurately horizontal and parallel to the plate 20. In addition a linear displacement transducer (LYDT) 23 is installed for detection of the sample deflection. As shown this is applied between the upper surface 27 of the plate 26 and a fixed point on the bar 13.

The modification to the conventional system therefore comprises the spring 25, the plate 26 and the rod 28 which introduces the spring in series between the sample 21 and the rigid beam 15 and its drive system.

In practice the clearance between the rod 28 and the opening 30 can be selected to be of the order of 0.010 millimeters and this ensures that the rod prevents the upper plate from vibrating and tilting during the loading/unloading cycle.

In operation the sample 21 which may be a single kernel of a seed product is positioned between the upper plate 20 and the lower plate 26. The deformation of the kernel is measured by the linear displacement transducer 23 and in one example this measurement can give accuracy of 0.05 percent in a transducer having a detection range of 5.08 millimeters. The control unit 19 can thus detect displacement as measured by the LVDT 23 and this can be recorded through the control unit onto a computer system using a diskette data acquisition system. Simultaneously the force acting upon the load cell and the displacement of the lower bar 15 are also recorded. The location of the bar 15 is communicated through the control unit by feedback from the motor 18.

The apparatus as described can be used to carry out various different experimental techniques including structural strength experiments.

In one experimental technique, the sample is exposed to a plurality of loading/unloading cycles and then a plurality of creep-recovery tests. In a second technique, the sample is subjected to only one creep-recovery test.

For all of these techniques, it is necessary to set on the control unit a required predetermined maximum force to be applied to the sample. The control unit thus has a manual input schematically indicated at 19A and the display schematically indicated at 19B. When the maximum force is input on the manual keypad 19A, the movement of the beam 15 is controlled by the control unit until the force as measured by the load cell 22 reaches the maximum at which time the motor is halted. When using the spring in series with the sample, the force acting on the sample is equal to the force acting on the spring. The properties of the spring that is the thickness of the spring material indicated at R, the spacing between the coils indicated at H and the length of the spring as indicated at L are selected correctly, the deformation of the spring is sufficiently large in comparison to the deformation of the investigative material so that the deformation of the sample as the proportion of the deformation of the spring is negligible. For this purpose the sample generally will have a diameter or longitudinal dimension less than five millimeters and the deformation of the sample will be less than five percent of the deformation of the spring for the maximum load intended to be applied.

Figure 2:
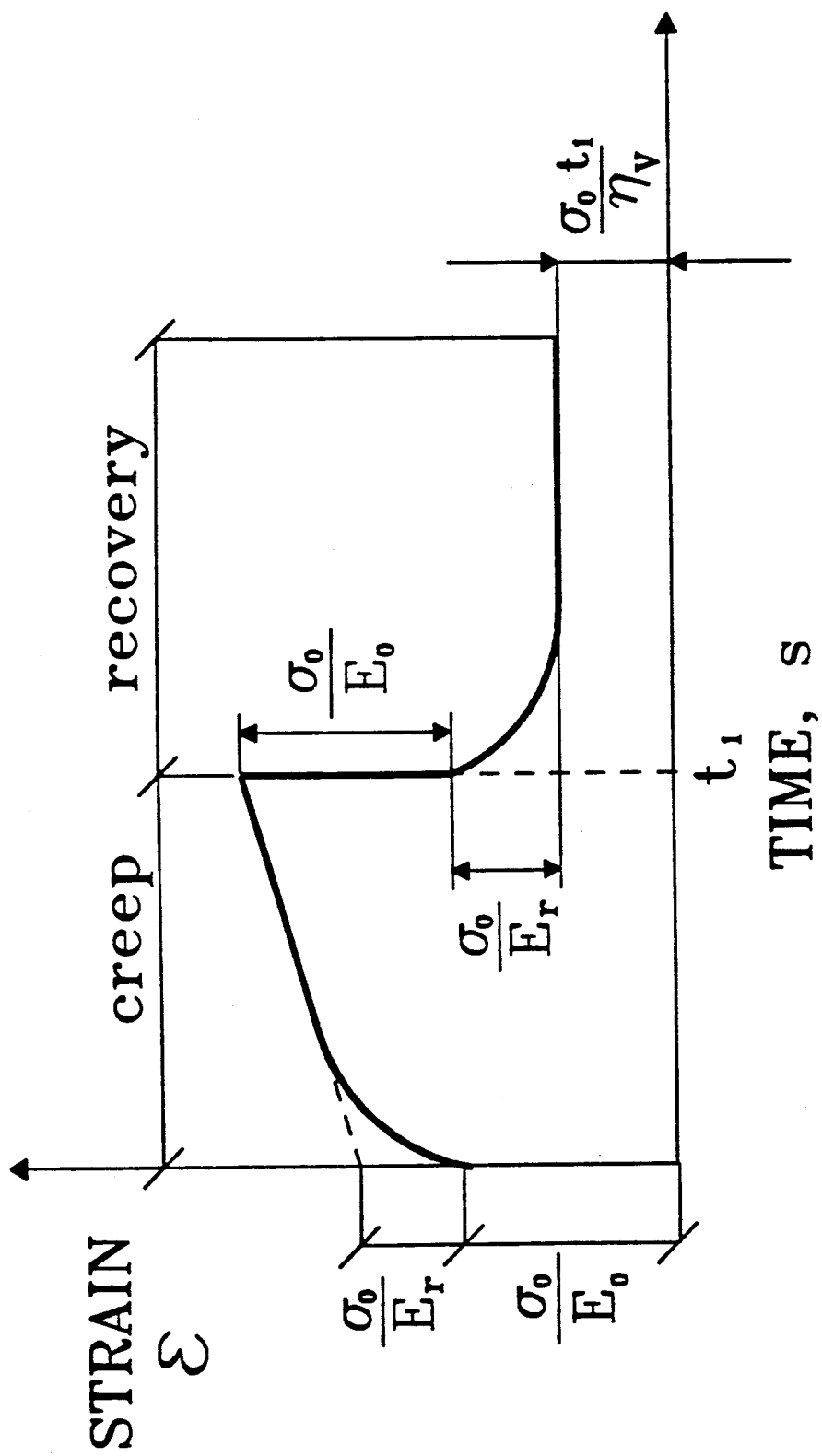
FIG. 2 is an example of a typical creep and recovery curve in a visco-elastic material.

In one example, wherein the sample comprises a kernel of canola, the intended actual maximum force would be of the order of 3.15 Newtons. In practice due to a tendency of the feedback system of the machine to overshoot, the upper limit is set at 3.00 Newtons (which overshoots to 3.15 Newtons) and a lower limit force is set at 0.15 Newtons which overshoots to 0.00 Newtons. The amount of overshoot is predictable and repeatable for a specific spring characteristics. The upward and downward velocity of the motor is set at 1.7 millimeters per second of movement of the lower bar 15. This velocity is sufficient within the accuracy of the experiment to simulate instantaneous application and removal of the force, as shown in FIG. 2. The kernel can then be subjected to a plurality for example 9 of creep-recovery tests using this experimental set up. Thus the kernel in suit with the spring is subjected to a constant or dead load of 3.15 Newtons for approximately 70 seconds and the kernel deformation is recorded. Then the load is released by moving the bar down until the minimum force acting on the kernel is obtained to ensure that the contact between the kernel and the load cell plate is maintained. The creep-recovery tests are performed with a break between succeeding tests.

FIG. 2 shows a typical creep-recovery curve of a visco-elastic material such as the canola seed sample described above.

Figure 3:
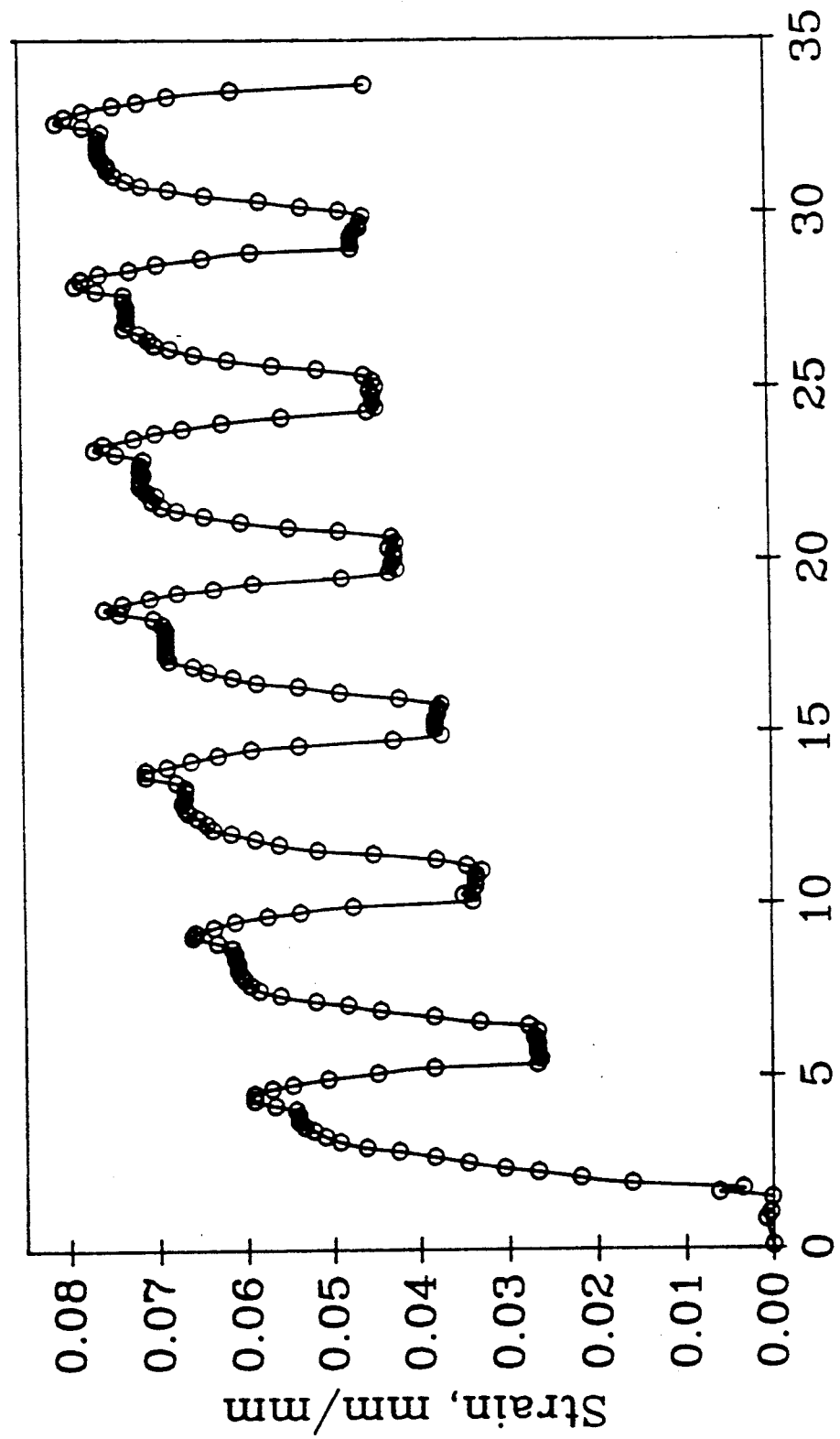
FIG. 3 is a typical graph of deformation versus time for a plurality of cycles of loading and unloading of the sample.

FIG. 3 shows a typical deformation curve for a plurality of loading and unloading cycles. These curves properly follow theoretical calculations and allow using the formulae available from those theoretical calculations for the calculation of various constants relating to the material. Thus, with the new method creep-recovery characteristics for small canola kernels were obtained for the first time.

As the load applied to the sample is directly proportional to the deformation of the spring indicated at L, the load applied can be detected by a deformation detection device (LvDT) schematically indicated at 35.

Since various modifications can be made in my invention as hereinabove described, and many apparently widely different embodiments of same made within the spirit and scope of the claims without departing from such spirit and scope, it is intended that all matter contained in the accompanying specification shall be interpreted as illustrative only and not in a limiting sense.

I claim:

1. A method for testing the mechanical properties of a sample of a solid material comprising providing a first abutment member having first means thereon for engaging the sample, providing a second abutment member having second means thereon for engaging the sample, placing the sample between the abutment members for application thereto of force in a longitudinal testing direction, moving the second abutment member relative to the first abutment member in said longitudinal testing direction to apply stress to the sample to cause strain in the sample, and measuring the stress and strain for analysis of the mechanical properties of the sample, wherein the movement of the second abutment member is applied from a movable element through a spring located between the movable element and the second abutment member so as to communicate force therebetween, the spring being elastically deformed during said movement and wherein the method includes the steps of driving the movable element with a motor in a direction to increase the force and at a rapid rate to simulate instantaneous application of the force, detecting the force with a load cell separate from the spring, automatically controlling the motor in dependence upon the detected force so as to halt the motor upon reaching a predetermined required maximum force, maintaining the motor halted for a predetermined period of time so as to provide a period for creep of the sample during which the sample is maintained under a substantially constant dead load, after said period of time driving the movable element with said motor in a direction to decrease the force and at a rapid rate to simulate instantaneous removal of the force so as to allow recovery of the sample, the spring being selected such that the amount of elastic deformation of the spring at the beginning of the creep period is greater than the amount of deformation of the sample which occurs during the creep period by a factor sufficiently large to maintain the assumption of a constant dead load during the creep period.

2. A testing method according to claim 1 wherein the spring comprises a coil spring having a central axis of the coil spring parallel to said longitudinal testing direction.

3. A testing method according to claim 1 wherein the movable element is driven by a lead screw and wherein deformation of the sample is measured by a linear detection device connected between the second abutment member and a fixed point on the first abutment member.

4. A testing method according to claim 1 wherein the deformation of the sample is less than five percent of the deformation of the spring.

5. A testing method according to claim 1 wherein the dimension of the sample in the longitudinal testing direction is less than five millimeters.

6. A testing method according to claim 1 wherein each of the first and second abutment members includes a respective sample engaging surface with the surfaces being parallel and at right angles to the longitudinal testing direction for compression of the sample between the surfaces, the spring comprising a compression spring having one end of the spring engaging the second abutment member at a surface parallel to the contact surface thereof and extending therefrom longitudinally of said longitudinal testing direction and engaging the movable element at a surface thereof parallel to said surfaces.

7. A testing method according to claim 6 including guide means for guiding movement of the second abutment member in a direction parallel to said longitudinal testing direction.

8. A testing method according to claim 1 including measuring the deflection of the spring to determine the force applied thereby to the second abutment member.

* * * * *